United States Patent [19]

Dürr et al.

[11] Patent Number: 5,723,031
[45] Date of Patent: Mar. 3, 1998

[54] METHOD FOR THE ANALYTICAL SEPARATION OF VIRUSES

[75] Inventors: Hansjörg Dürr, Burscheid; Hans-Robert Hehnen, Siegburg; Lothar Helbig; Roberto Correa, both of Leverkusen; Ulf Brüggemeier, Leichlingen, all of Germany

[73] Assignee: Bayer Aktiengesellschaft, Leverkusen, Germany

[21] Appl. No.: 547,765

[22] Filed: Oct. 24, 1995

[30] Foreign Application Priority Data

Oct. 31, 1994 [DE] Germany ............... 44 38 833.0

[51] Int. Cl.$^6$ ............... G01N 27/26; G01N 27/447
[52] U.S. Cl. ............... 204/451; 204/601
[58] Field of Search ............... 204/451, 452, 204/453, 454, 455, 601, 602, 603, 604, 605

[56] References Cited

U.S. PATENT DOCUMENTS

| | | | |
|---|---|---|---|
| 4,181,589 | 1/1980 | Brooks | 435/173.9 |
| 4,783,419 | 11/1988 | Hayashi et al. | 204/549 X |
| 5,045,172 | 9/1991 | Guzman | 204/452 |
| 5,108,568 | 4/1992 | Van Alstine | 204/450 |
| 5,274,240 | 12/1993 | Mathies et al. | 204/452 X |
| 5,324,401 | 6/1994 | Yeung et al. | 204/452 |

FOREIGN PATENT DOCUMENTS

WO 95/08640  3/1995  WIPO.

OTHER PUBLICATIONS

Y. Baba, et al., Trends in Analytical Chemistry, vol. 11, No. 8, pp. 280–287, (1992) *no month available.

D.H. Shain, et al., Analytical Biochemistry, vol. 200, pp. 47–51, (1992) *no month available.

Hjertén et al., *Carrier–Free Zone Electrophoresis, Displacement Electrophoresis and Isoelectric Focusing in a High–Performance Electrophoresis Apparatus*, Journal of Chromatography, 403 (1987) 47–61 *no month available.

Stellan Hjerten et al, "Carrier–Free Zone Electrophoresis, Displacement Electrophoresis and Isoelectric Focusing In a High–Performance Electrophoresis Apparatus" Journal of Chromatography, 403 (1987) *no month available 47–61.

William M. Hurni and William V. Miller, "Analysis of a vaccin purification process by capillary electrophoresis" Journal of Chromatography 559 (1991) 337–343 *no month available.

*Primary Examiner*—Kathryn L. Gorgos
*Assistant Examiner*—John S. Starsiak, Jr.
*Attorney, Agent, or Firm*—Sprung Kramer Schaefer & Briscoe

[57] ABSTRACT

The method permits the non-destructive analytical detection and/or the quantification of viruses or viral particles (analytes) in a liquid sample matrix containing organic or inorganic minor constituents, in particular protein moieties and/or nucleotides and/or other viruses. To this end the viruses or the viral particles are separated from the protein moieties and/or nucleotides in the sample matrix using capillary electrophoresis and at the same time the electropherogram associated therewith is recorded. The fractions assigned to the analytes can then be identified as virus peaks in the electropherogram by spectroscopic interpretation with the aid of characteristic maxima. For better identification, a reference sample of a known virus or of a known viral particle can be added to the sample matrix.

5 Claims, 11 Drawing Sheets

Fig. 1(a)
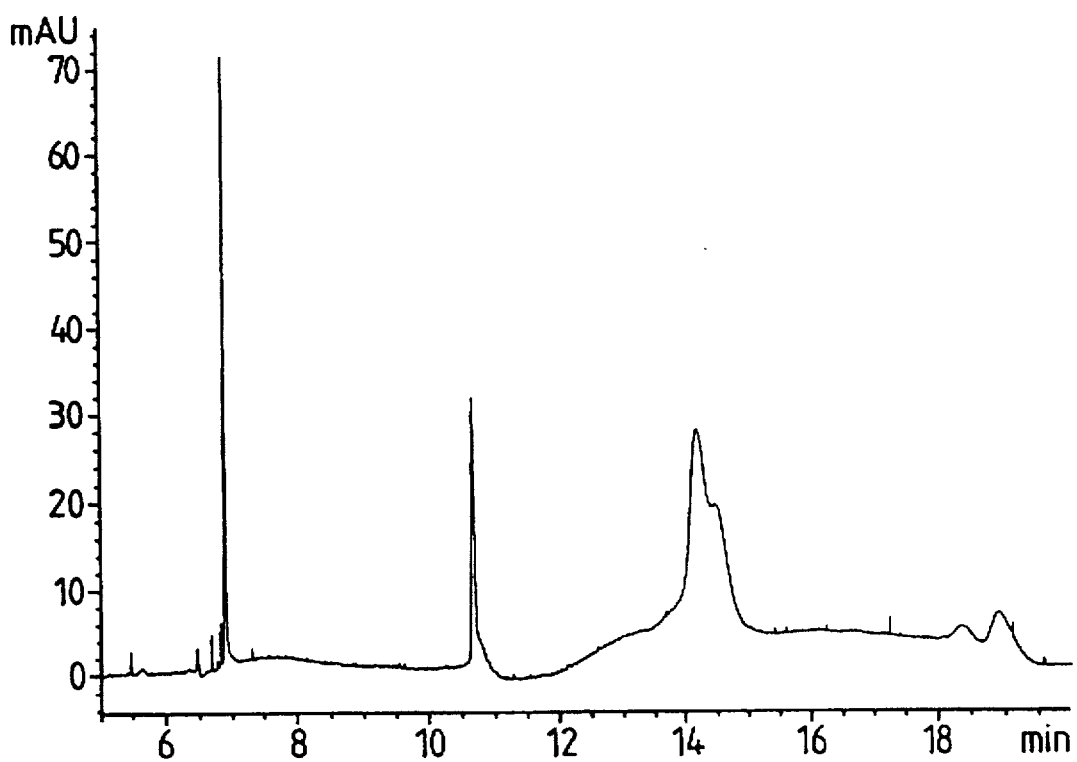
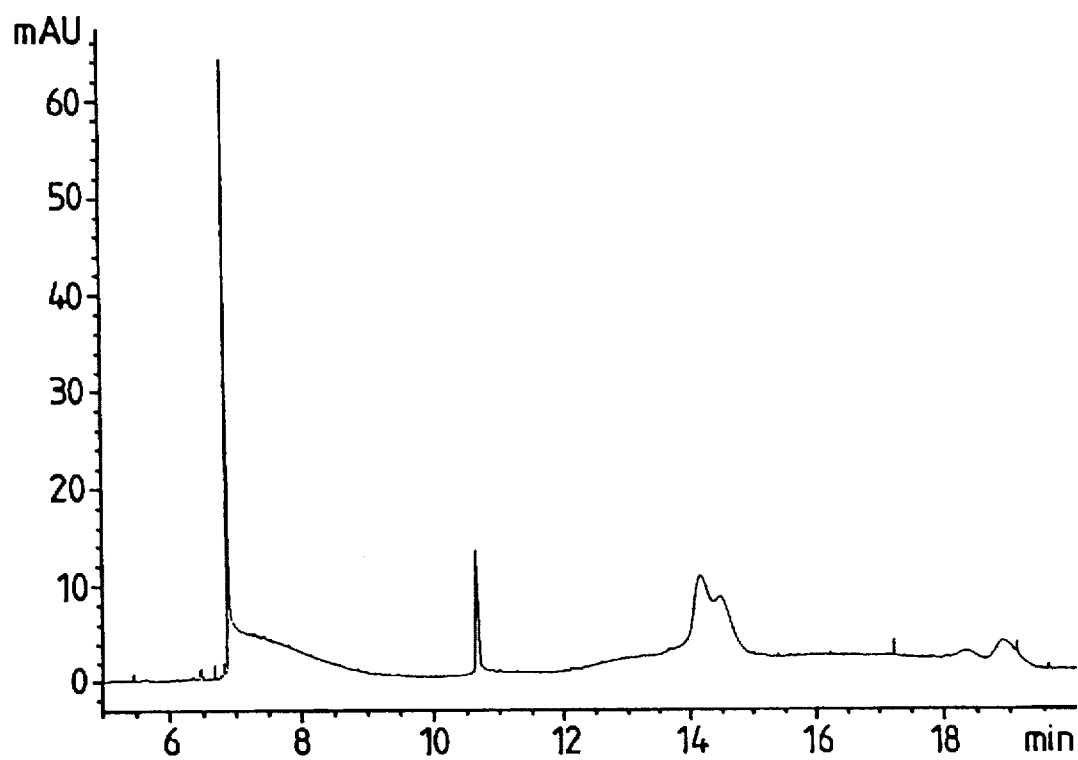
Fig. 1(b)

Fig. 3 (a)
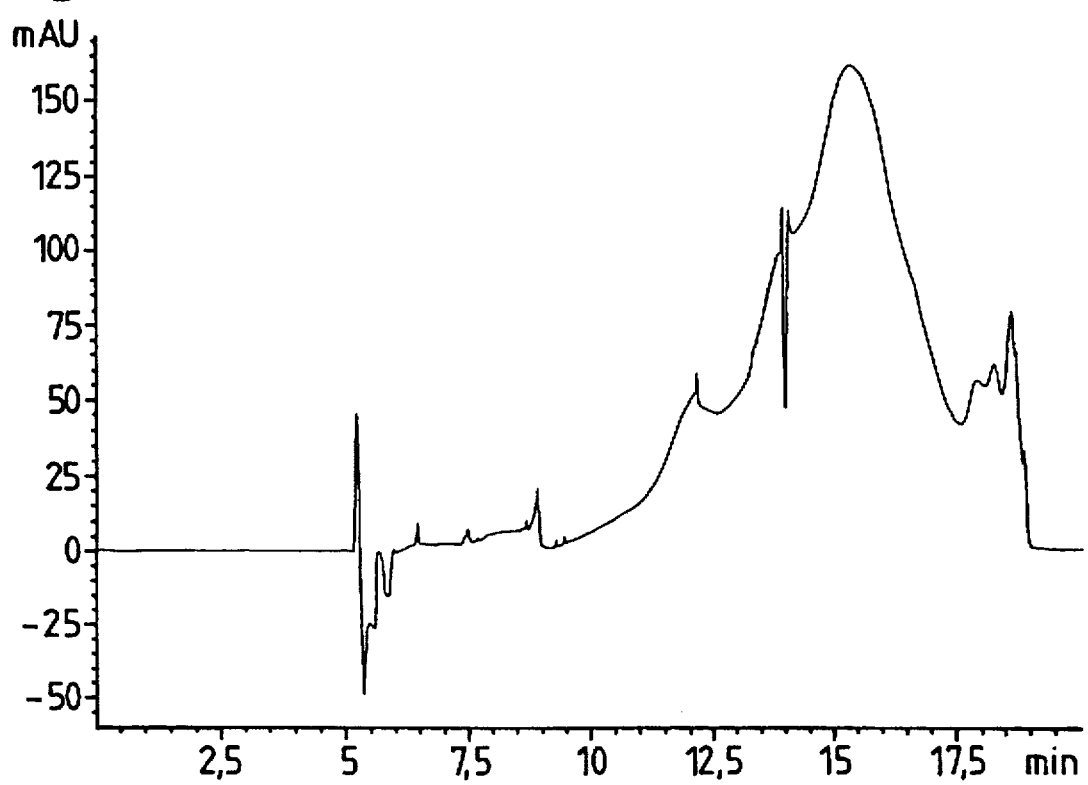
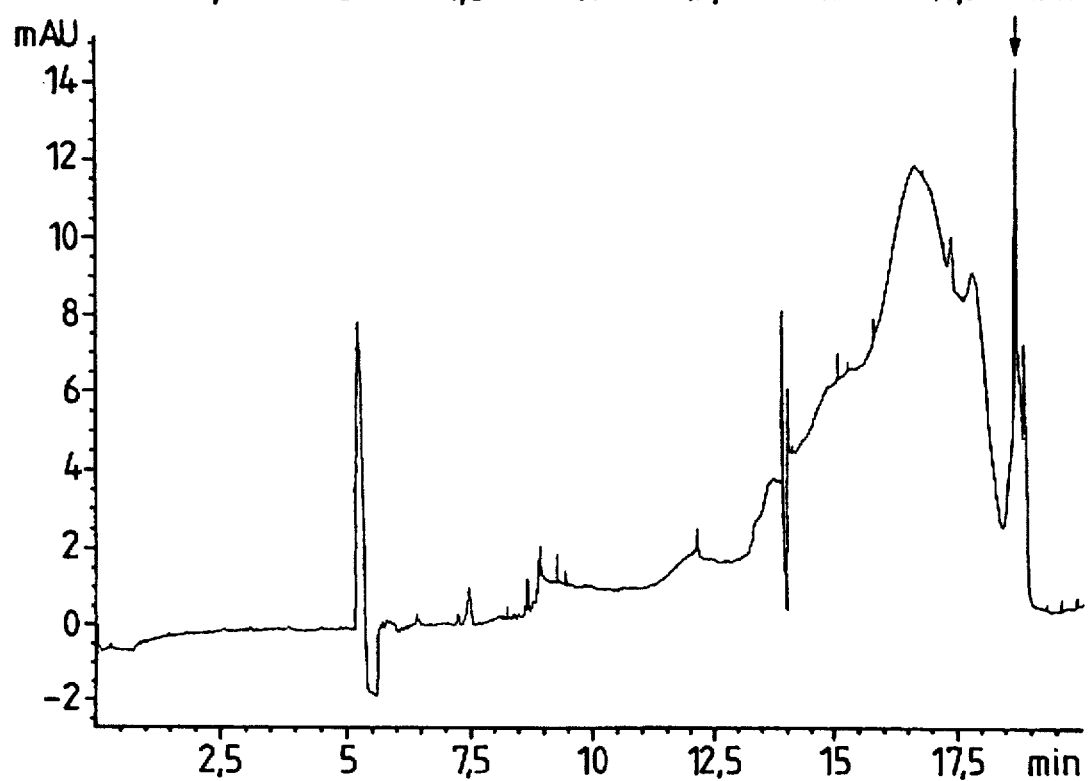
Fig. 3 (b)

Fig. 4 (a)
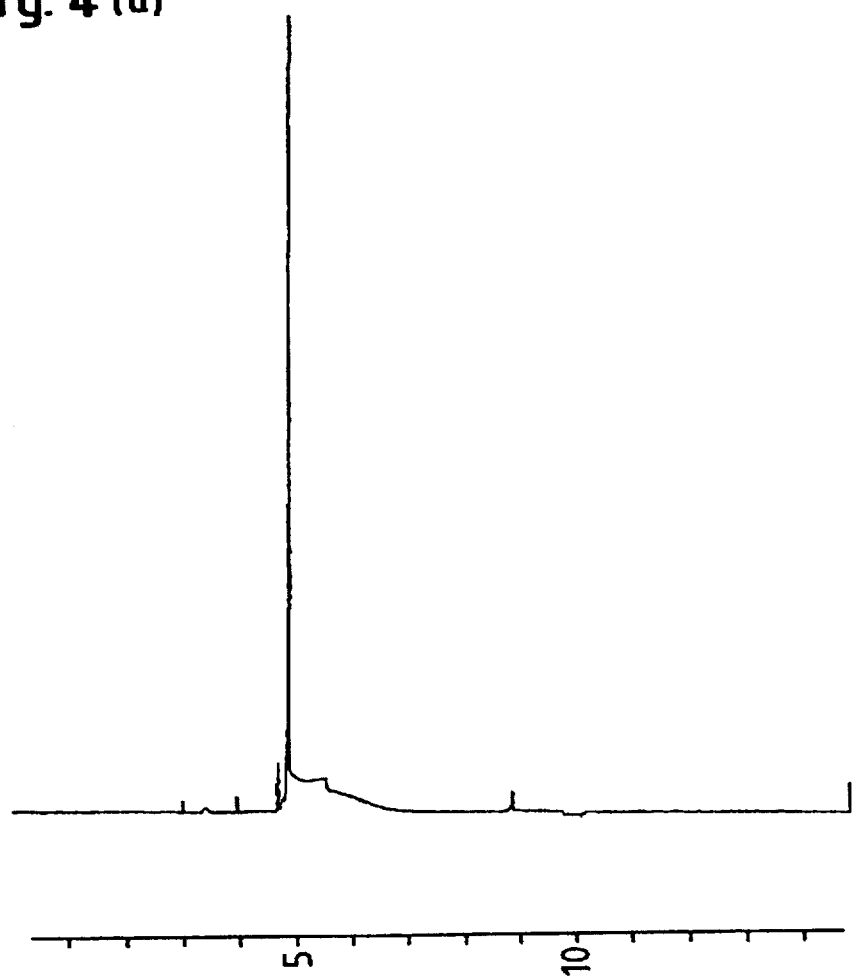
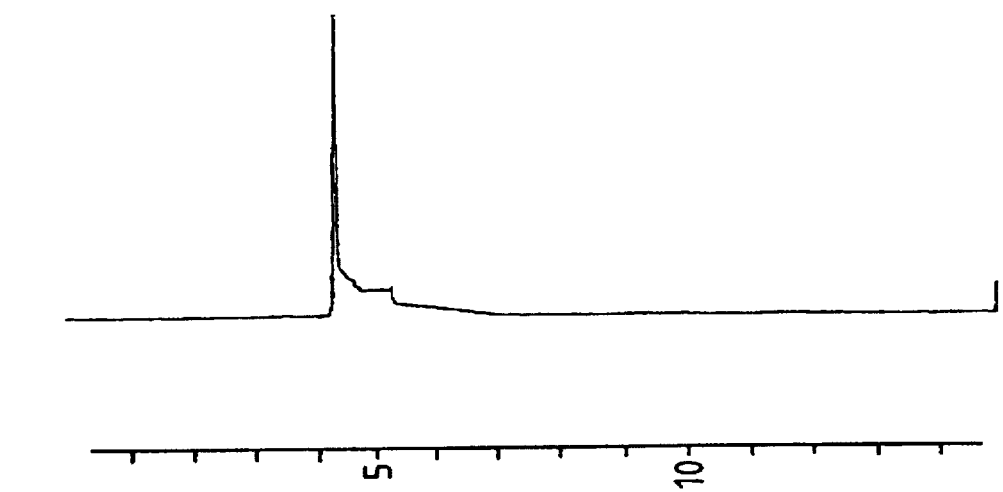
Fig. 4 (b)

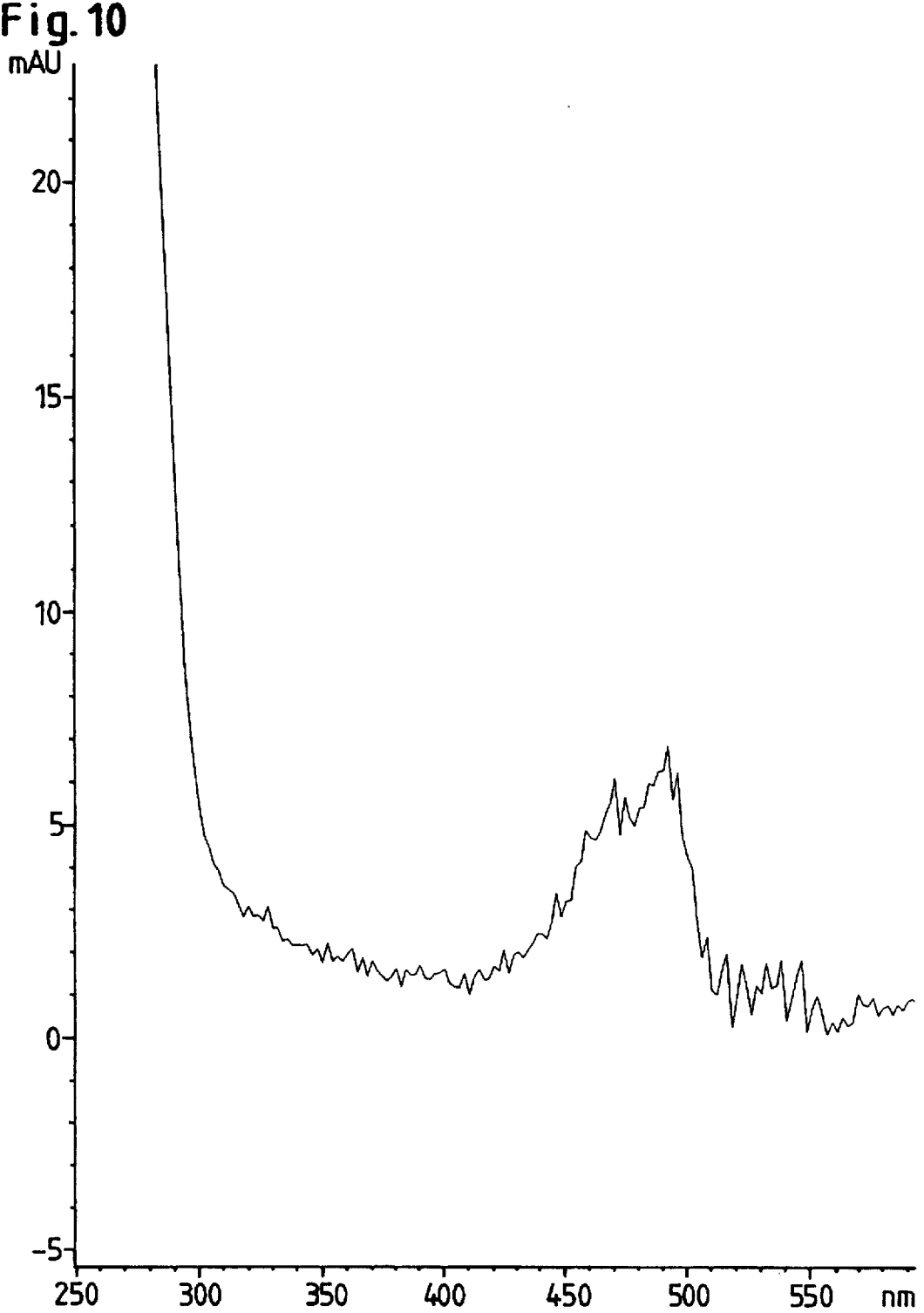

Fig. 11 (a)
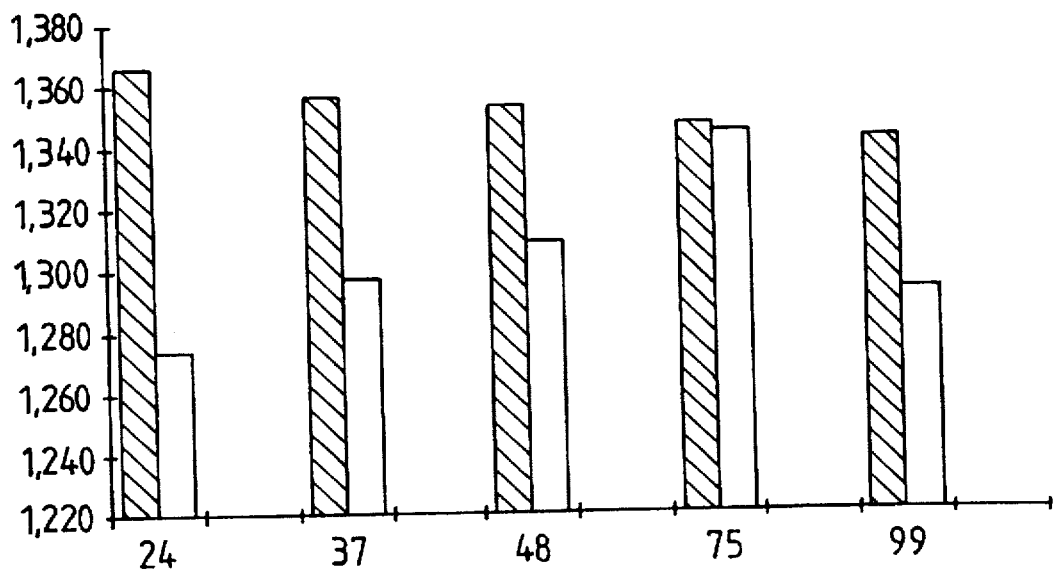
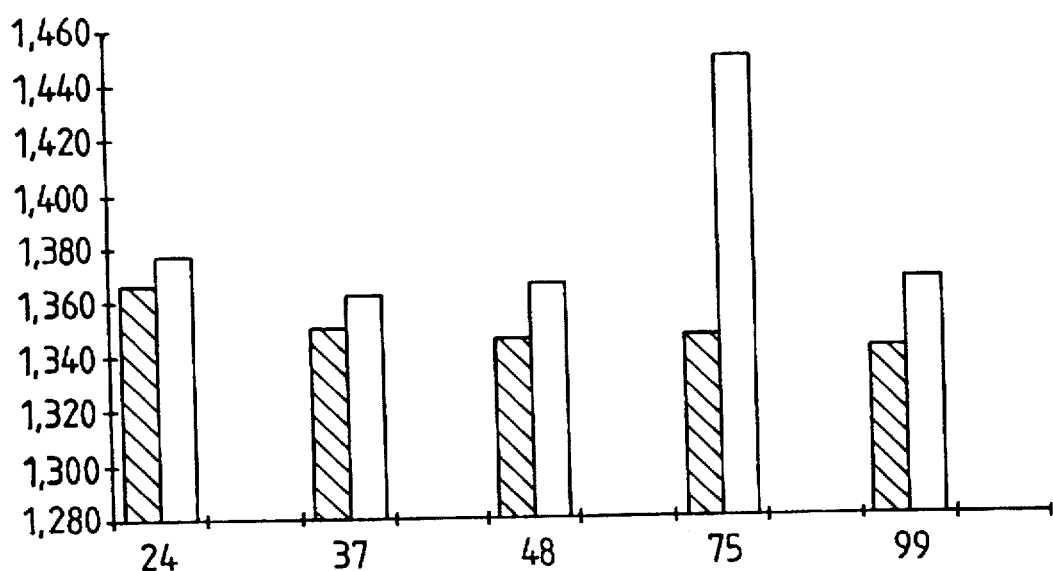
Fig. 11 (b)

METHOD FOR THE ANALYTICAL SEPARATION OF VIRUSES

The invention relates to a method for the non-destructive analytical detection and/or for the quantification of viruses or viral particles (analytes) in a liquid sample matrix containing organic or inorganic minor constituents, in particular protein moieties and/or nucleotides and/or other viruses.

Immunological methods which are based on specific antigen-antibody interactions are known. The numerous applied methods such as, for example, ELISA (Enzyme-Linked-Immuno-Sorbent-Assay), complement binding reaction, SNT (Serum Neutralisation Test) and fluorescence-labelled antibodies differ only in the detection method.

The problem with these methods is the high specificity of the detection reaction to the immunogenic region of the virus. It is also not possible to distinguish between the antigen activity of the virus particle and that of the immuno-reactive protein. Conversely false positive results or cross-reactivities can also appear.

The specific viral activity is usually measured from the two following effects.

a) A specific pathogenic effect of the virus on target cells is identified.

For example, the visual inspection of an infected cell population for cytopathogenicity, haemagglutination or haemadsorption may be mentioned here.

b) A virus-specific enzyme reaction can, for example, be measured in retroviruses via the reverse transcriptase activity.

The problem here is the poor quantifiability and the uncertainty in the relevance of the test systems for the transferability to the natural host.

Molecular biological methods can be summarised as follows.

a) In probe diagnostics viral nucleotide sequences are identified by hybridisation with specific introduced gene probes.

b) Viral genes are identified by a specific cleaved sample produced by restriction enzymes.

c) Viruses are identified by the amplification of specific gene sequences (PCR).

d) Viral genes are identified by nucleotide sequencing.

These methods encompass the greatest amount of information for the identity of a virus. They are however relatively expensive, labour-intensive and not very suitable for quantification. Moreover these analytical techniques describe the genotype and not the phenotype of the virus.

The virus-specific protein pattern can be identified by separation using various electrophoretic and chromatographic techniques. Immunogenic proteins can in addition be recognised by immunological methods (immunoblot). Viruses have to be very clean prior to cleavage (involving purification costs) in order that the protein bands can be classified. Viruses which are already broken down can also show the correct pattern.

Capillary electrophoresis (CE) is a relatively new separating technique whereby the sample to be analysed is separated in a capillary in an electrical high-voltage field owing to different migration rates. The detection takes place directly in the capillary with the use of optical detectors [1]. The range of application of CE is very wide and extends over ion analysis, separation of enantiomers, protein analysis and nucleotide analysis down to the separation of particles [2]. Hitherto only individual molecules or uniform, mechanically stable particles have been investigated by this technique. For example, the separation of recombinant lipoprotein particles by capillary electrophoresis is described in [3].

For sensitive fluorescence detection, DNA/RNA-binding staining reagents are successfully used for DNA and RNA [4, 5]. These stains to some extent show differing selectivities for single-stranded or double-stranded nucleotides or differing fluorescence maxima for RNA and DNA. Thus, for example, acridine orange shows a maximum in the fluorescence emission at 520 nm for DNA and at 650 nm for RNA. Fluorescence detection is also described in CE almost exclusively for double-stranded DNA [6].

A large number of methods for protein-ligand interactions for the determination of binding constants using CE have been described in the literature [7, 8]. The methods are based either on a shift in migration time through the interaction, or on alterations in the peak area, of an interacting participant. This can be effected experimentally in the following ways.

1. The interacting participants are incubated prior to the CE separation and the complexes formed are separated from the individual components using CE.
2. An interacting participant is placed in the CE buffer and the shift in migration time of the other participant is measured (affinity capillary electrophoresis).

The first method has the advantage of being economical with material and variable as to the choice of the interacting participants and was therefore primarily investigated.

The invention is based on the object of improving the analytical investigation of viruses, so that a rapid and definite identification and/or quantification in a liquid sample matrix containing organic or inorganic minor constituents, in particular protein moieties and/or nucleotides, is rendered possible.

This object is fulfilled according to the invention using a method whereby the viruses or the viral particles are separated from the protein moieties and/or nucleotides in the sample matrix using capillary electrophoresis and at the same time the electropherogram associated therewith is recorded and the fractions assigned to the analytes are identified as virus peaks in the electropherogram by spectroscopic interpretation with the aid of characteristic maxima.

Viral particles are by definition active and inactivated viruses, as well as chemically, molecular biologically or enzymically modified particles, which owing to their surface properties, or owing to their structural make-up, are to be regarded as virus-like. The viruses (viral particles) may contain DNA or RNA, double-stranded or single-stranded and may be present coated or uncoated. The separation does not depend on the size of the virus; viroids or virions can also be characterised in this way.

The viruses can be identified directly from any sample matrix, for example, from biological material (serum, urine, cells, plasma, cell supernatant, aqueous humour, saliva, et cetera) or from non-biological formulations (water, medicaments, soil samples, et cetera).

A reference sample of a known virus or of a known viral particle is advantageously added to the sample matrix for identification.

Preferably the viruses or the viral particles are stained with a RNA/DNA-binding, spectroscopically identifiable stain.

A particularly high sensitivity can be achieved if a fluorescent stain is used, which is detected by fluorescence spectrometry.

A further improvement consists in incubating the virus or the viral particles with specific antibodies which give rise to a shift in the electrophoretic migration time or an alteration in the virus peak.

By means of the new method the production of viruses can advantageously be monitored and controlled by measuring techniques during the manufacture of vaccines.

Another, very important application is that viruses can be diagnosed directly in biological materials, in body fluids in particular.

The following advantages are gained by using the method according to the invention.

Compared with the existing analytical techniques the separation of the viral particles by capillary electrophoresis excels in the simple sample preparation, the short analysis times, the exact quantifiability, the possibility of automation, the possibility of standardisation and the additional quality of the information, as for the first time an identification and quantification of intact viruses without qualification is possible.

These advantages have a particularly great effect:

a) In Process Control

Using this method it is possible for the first time, because of the rapid and quantitative analysis, not only to monitor the process but also to control it during the manufacture of vaccines.

b) In Product Control

By this means for the first time the quality assurance of the end product, from the formulation to the supervision of the storage stability and of the transport conditions, can be carried through using a standardised method.

c) In the Diagnosis of Viruses

Using this method viruses can for the first time be directly detected and identified. This is of great importance both for product monitoring during the production of viruses and to ensure freedom from viruses in biological materials.

d) In Monitoring Therapy

When antiviral therapeutic agents are used, the outcome of therapy can be monitored directly.

e) In the Identification of Viruses

Owing to the differing electrophoretic properties of the viruses and the specific detectability thereof in the capillary, known viruses can be identified and unknown viruses can be established. Several (different) viruses (strains of viruses) can also be identified in parallel in this way.

The procedure whereby viruses and viral particles can be separated by capillary electrophoresis, directly identified and quantified using the new analytical technique is described below with the aid of Examples using measuring curves.

BRIEF DESCRIPTION OF THE DRAWINGS

FIGS. 1(a and b): shows a capillary electropherogram of an inactivated foot-and-mouth reference sample, detection at 210±8 nm (a) and 257±8 nm (b). The virus signal can be identified by the increase in the detection at 257 nm.

FIGS. 3(a and b): shows a capillary electropherogram of inactivated foot-and-mouth concentrate. Detection at 210±8 nm (a) and 257±8 nm (b). The virus is indicated by the arrow.

FIGS. 4(*a* and *b*): shows a comparison of the CE separations of inactive (a) and active (b) foot-and-mouth reference samples. Detection at 257 nm.

FIG. 5: shows CE separation of stained, inactivated foot-and-mouth virus from FIG. 1. Detection at 257±8 nm. The signal at 3.8 min could be assigned to excess ethidium bromide from the incubation. The virus signal was not shifted by the staining (Comparison with FIG. 1).

FIG. 6: shows DAD spectra of ethidium bromide (a) and of the stained, inactivated foot-and-mouth virus (b) from FIG. 5. The successful staining of the virus could thus be proved. The virus signal was also specified thereby.

FIG. 7: shows CE separation of stained (YOYO), inactive foot-and-mouth concentrate from FIG. 3 using LIF detection. Out of the complex mixture (FIG. 3) only the virus is still detectable and is detected with distinctly greater sensitivity.

FIGS. 8(*a* and *b*): shows a comparison of CE separations of inactive orf virus prior to (a) and after incubation using an orf-specific MAB (b). The virus was stained with YOYO and detected by LIF.

FIGS. 9(*a* and *b*): shows CE separations of the core of the orf virus after staining with YOYO and detection at 257 nm (a) and LIF detection (b). The broad signal at 257 originates from excess YOYO. The different migration times result from different separating conditions.

FIG. 10: shows DAD spectrum of the core of the orf virus with intercalated YOYO from FIG. 9. An absorption maximum in the excitation region of the argon laser of the LIF detector (495 nm) was produced by intercalation.

FIGS. 11(*a* and *b*) shows a comparison of the relative migration times of foot-and-mouth $O_{1k}$ (a) and foot-and-mouth $O_{1m}$ (b) without MABs (dark bars) and after incubation with different anti-foot-and-mouth $O_1$ MABs (light bars).

GENERAL DESCRIPTION OF THE METHOD

The sample to be analysed is introduced in liquid form (solution, suspension) into a capillary which has been previously rinsed with the separating buffer or filled with a buffer system. The transport of the flow is ensured at both ends of the capillary by direct contact, or via a conductive buffer, and an electric field is produced in the capillary through the application of a high voltage. The viruses are separated in the electric field. The direct identification of the viruses in the capillary is carried out by detecting the UV absorption at one or more wavelengths. As viruses are composed both of proteins and of nucleotides, virus-specific detection is possible by detection at 256–260 nm (maximum for nucleotide absorption) and 210, 280 nm (protein absorption). In the case of very large viruses the light scattering prevents direct identification by UV absorption (cf. Example 2.3). In the case of known viruses, however, light scattering can be used for identification and quantification. The separating buffer in the capillary is adjusted to the task of separation and the stability of the virus (pH value, ionic strength, detergents, additives). The required apparatus is any CE device having an optical detector. The sample can be introduced into the capillary electrokinetically, hydrodynamically, or by vacuum injection or application of pressure. There are no restrictions as regards the capillary (fused silica capillary, coated or uncoated, teflon or any other organic or inorganic material). The diameter of the capillary is also irrelevant to the separation and limited only by the electrophoretic conditions (transport of the flow, detectability, dissipation of heat).

Examples

1. Separation and Direct Identification of Foot-and-Mouth Viruses

Foot-and-mouth viruses belong to the group of the Picornaviruses and have an icosahedral surface structure which is built up from four virus proteins. The diameter is approx. 25 nm. Inside there is a single-stranded RNA having a length of approx. 5000 bases.

The propagation and isolation of the viruses is summarised in Table 1.

TABLE 1

Isolation of foot-and-mouth virus

| | |
|---|---|
| Virus propagation | BHK-21 suspension cells in fermentation cultures up to 1,500 l, harvest of viruses after cell lysis |
| Preliminary purification | Preclarification of the raw virus suspension by low-speed continuous centrifugation |
| Inactivation | Ethylene imine (in situ from bromoethylene amine and NaOH) |
| Preparation of concentrate | PEG precipitation and resuspension in 1/100 of the original volume |
| Purification of reference samples | CsCl density-gradient centrifugation for isolation of 146S particles (whole, inactive viruses) |

Example 1.1: Identification of an Inactivated Foot-and-Mouth Virus

Figure 2:
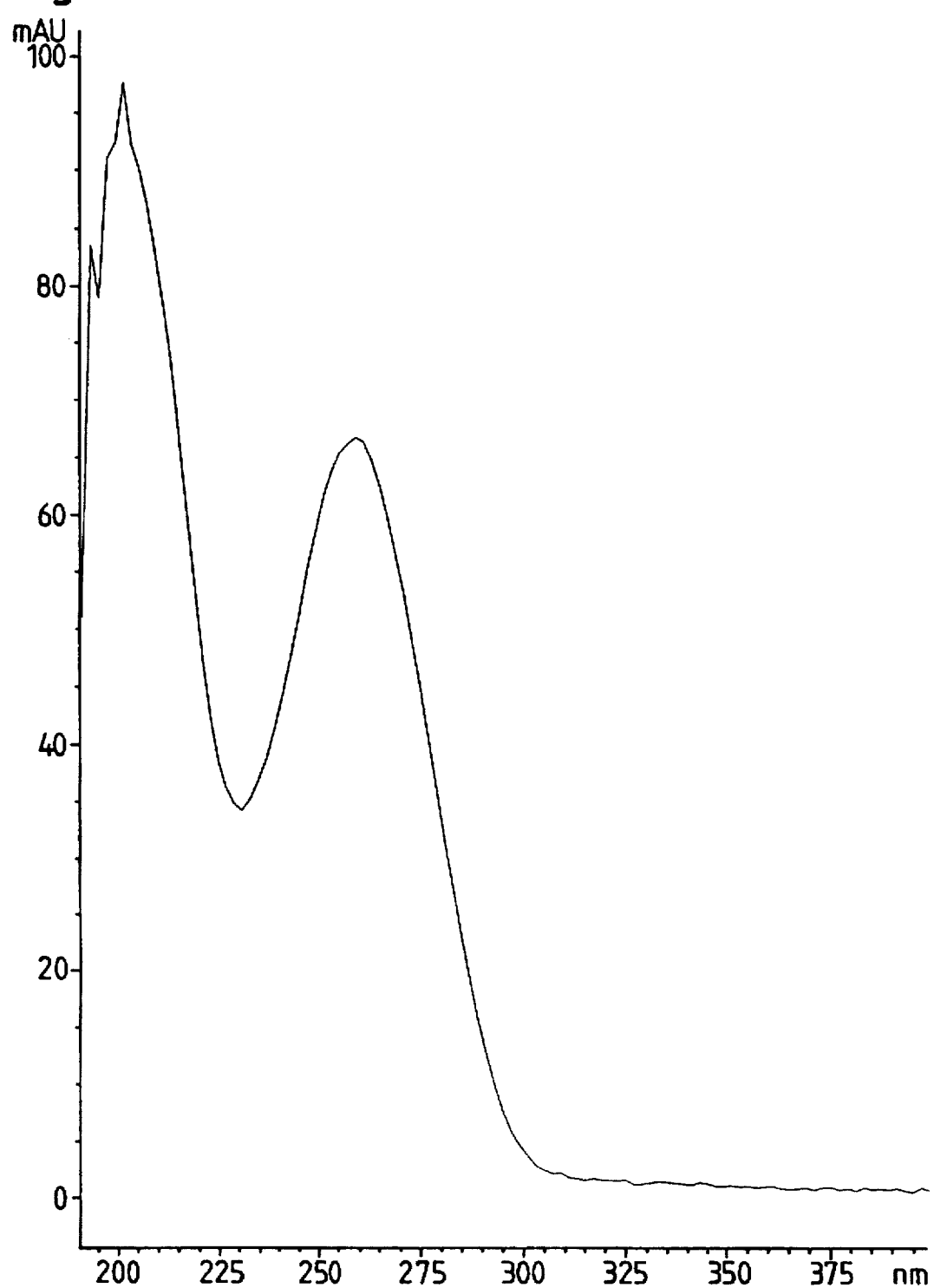
FIG. 2: shows a DAD spectrum of the inactivated foot-and-mouth virus from FIG. 1.

A reference sample (cf. Table 1) (100 µg/ml) was separated by capillary electrophoresis in a capillary electrophoresis apparatus from the firm Hewlett-Packard (Type $^{3D}$HPCE). The measuring conditions are summarised in Table 2. The associated electropherogram is shown in FIG. 1. The sharp signal at 6.9 min clearly emerges at the transition from 210 to 257 nm. The UV spectrum of this signal was recorded directly from FIG. 1 by means of a diode array detector (DAD). The maximum at 256 nm is characteristic for nucleotides, whereas the intensive short-wave maximum and the gradual fall to 300 nm can be explained only by additional protein moieties (FIG. 2). The UV spectrum measured in the capillary was identical with the UV spectrum of the isolated virus and could consequently be utilised for the direct identification of the virus signal. None of the minor constituents in FIG. 1 showed a similar UV spectrum and therefore did not represent any intact virus particles either.

TABLE 2

Measuring conditions for the direct identification of foot-and-mouth reference samples by means of CE

| | |
|---|---|
| Capillary: | Fused silica capillary, 75 µm internal diameter, 64.5 cm length, 56 cm to the detector |
| Voltage: | 20 kV |
| Buffer: | Tris (25 mmolar), glycine (192 mmolar) pH 8.5 |
| Temperature: | 25° C. |
| Detection: | DAD 190–600 nm, $\lambda_1$ 210 ± 8 nm, $\lambda_2$ 257 ± 8 nm |
| Injection: | Pressure (20 sec × 5 × 10$^3$ Pa) |
| Rinsing of the capillary prior to injection: | 1. NaOH (0.1 N, 1 min, 5 ×0 10$^4$ Pa) 2. Buffer (3 min, 5 × 10$^4$ Pa) |

Example 1.2: Separation and Identification of the Inactivated Foot-and-Mouth Virus From a Complex Sample Matrix The inactivated virus could be identified directly (FIG. 3, measuring conditions in Table 3) in the concentrate (cf. Table 1). As expected, a complex electropherogram appeared at 210 nm. The biological background became distinctly lower from 210 to 257 nm and the sharply emerging signal indicated a significant nucleotide content. The virus signal (arrow) could be identified via the UV spectrum and by coinjection using the corresponding reference sample (no figure). A simpler and direct identification is shown in Example 2.2.

TABLE 3

Measuring conditions for the direct UV spectroscopic identification of foot-and-mouth viruses from raw concentrates

| | |
|---|---|
| Capillary: | Fused silica capillary, 50 µm internal diameter, 64.5 cm length, 56 cm to the detector |
| Voltage: | 20 kV |
| Buffer: | Tris (25 molar), glycine (292 mmolar), sodium dodecyl sulphate (50 mmolar), pH 8.5 |
| Temperature: | 25° C. |
| Detection: | DAD 190–600 nm, $\lambda_1$ 210 ± 8 nm, $\lambda_2$ 257 ± 8 nm |
| Injection: | Pressure (20 sec × 5 × 10$^3$ Pa) |
| Rinsing of the capillary prior to injection: | 1. NaOH (0.1 N, 1 min, 5 × 10$^4$ Pa) 2. Buffer (3 min, 5 × 10$^4$ Pa) |

Example 1.3: Separation and Identification of Active Foot-and-Mouth Virus

Reference samples from the virus material were purified before and after inactivation (cf. Table 1). The activity of the virus was examined by titration in BHK cell cultures (titre>10$^7$ KID$_{50}$). Both samples (active and inactive) were adjusted to the same quantity of 146S particles and separated by means of a capillary electrophoresis apparatus from the firm Perkin Elmer (Type ABI 270 A-HT) (measuring conditions are given in Table 4). The detection at 257 nm showed comparable electropherograms for both preparations (FIG. 4). The active and inactive virus could not be separated by means of CE. As the inactivating reagent is also preferably reacted with the RNA in the interior of the foot-and-mouth virus, an alteration of the surface charge condition critical for the CE separation was not to be expected either.

TABLE 4

Measuring conditions for the CE separation of reference samples of active foot-and-mouth viruses

| | |
|---|---|
| Capillary: | Fused silica capillary, 50 µm internal diameter, 72 cm length, 51 cm to the detector |
| Voltage: | 20 kV |
| Buffer: | Tris (25 mmolar), glycine (192 mmolar), pH 8.5 |
| Temperature: | 35° C. |
| Detection: | UV 257 nm |
| Injection: | Vacuum (5 sec × 17 × 10$^3$ Pa) |
| Rinsing of the capillary prior to injection: | 1. NaOH (0.1 N, 1 min, 68 × 10$^3$ Pa) 2. Buffer (3 min, 68 × 10$^3$ Pa) |

Examples 1.1–1.3 clearly show the suitability of this new analytical technique for the direct identification both of active viruses and of inactivated viral particles (inactivated samples). Even complex sample matrices, which occur for example in the concentrate, do not interfere with the separation. Here the high separation efficiency of capillary electrophoresis and the good matrix compatibility of the analytical technique, which is free from solid-phase separating material, take effect to great advantage. The universally new method could be successfully demonstrated and used by means of these Examples. Viruses can be directly detected and identified using this new analytical technique.

The peak area of the virus signal correlates with the quantity of the virus and for this reason is suitable for the direct quantification of the virus concentration. The Example of the foot-and-mouth virus showed that the UV absorption could be used for the direct identification of the virus signal. In the case of very large viruses, the light scattering prevents direct identification by UV absorption. Moreover the detection limit for UV-absorbing viruses is in the microgram per milliliter range (>$10^6$ particles/ml) and therefore inadequate for many purposes. In the next section methods will be presented which provide a specific detection system for these viruses as well.

2. Identification of Viruses Using a RNA/DNA Specific Detection System Based on DNA/RNA-Binding Stains The means whereby DNA/RNA-binding stains can be used for the direct staining of viruses is described below. In an extension of the separation method for viruses and viral particles explained under Section 1, it is also described firstly, how the allocation of the signal, especially in complex systems, is considerably facilitated, if not even made possible for the first time and secondly, how a further specification and above all an extreme increase in sensitivity is achieved by fluorescence detection.

The viruses stained in this way can be separated from other DNA/RNA-containing components by means of CE separation. The labelled virus can thus be directly identified. A further virus specification can be achieved via the selectivity of the stains for DNA or RNA, double-stranded or single-stranded respectively. Coated and uncoated viruses can also be differentiated via the differing rates of passage of the stains through the membranes.

Fluorescence detection, owing to the multiple incorporation of the stains (all 10 to 20 base radicals), results in an extreme increase in sensitivity. Statistically up to 15,000 stain molecules are thereby incorporated, each of which contributes to the fluorescence signal. Simply by calculation, for given viruses the detection limit using fluorescence detection is below that of a particle.

Thus for the first time stained viruses are separated using CE, identified with the aid of the characteristic UV absorption and detected with high sensitivity from the fluorescence. Using procedures based on the work in Examples 1.1–1.3, foot-and-mouth viruses were stained with DNA/RNA-binding stains and were analysed by means of CE and DAD detection. The long-wave absorption maxima of the stained viruses correspond to a first approximation to the absorption maxima of the stained, free RNA or DNA.

General Description of the Staining Process

The sample to be analysed is:

a) incubated with the DNA/RNA-binding stain and then separated and analysed according to the method described under Section 1 or b) the DNA/RNA-binding stain is added to the separating buffer and the virus is stained during the separation in the capillary. The virus with the DNA/RNA bound stain can be detected either by the specific UV/VIS absorption or by the specific extinction and emission of the fluorescence.

Examples

Of the numerous, successfully employed staining detection methods using different viruses and different stains, two different systems are represented here by way of example.

First of all the separation, identification and highly-sensitive detection of stained foot-and-mouth viruses is described.

Through staining with the DNA/RNA-binding stains, the short-wave absorption spectrum is shifted and in addition an absorption appears in the visible region. For the first time, therefore, UV absorption is to be used for detecting the successful separation of the stained viruses and moreover the virus is to be independently identified via the characteristic absorption spectrum.

Another complicating factor arises from the fact that foot-and-mouth viruses contain single-stranded RNA whereas the staining reagents have been developed for double-stranded DNA. Preliminary investigations show, however, that free single-stranded DNA and RNA, although to a lesser degree, can also be stained and detected by means of CE.

Figure 5:
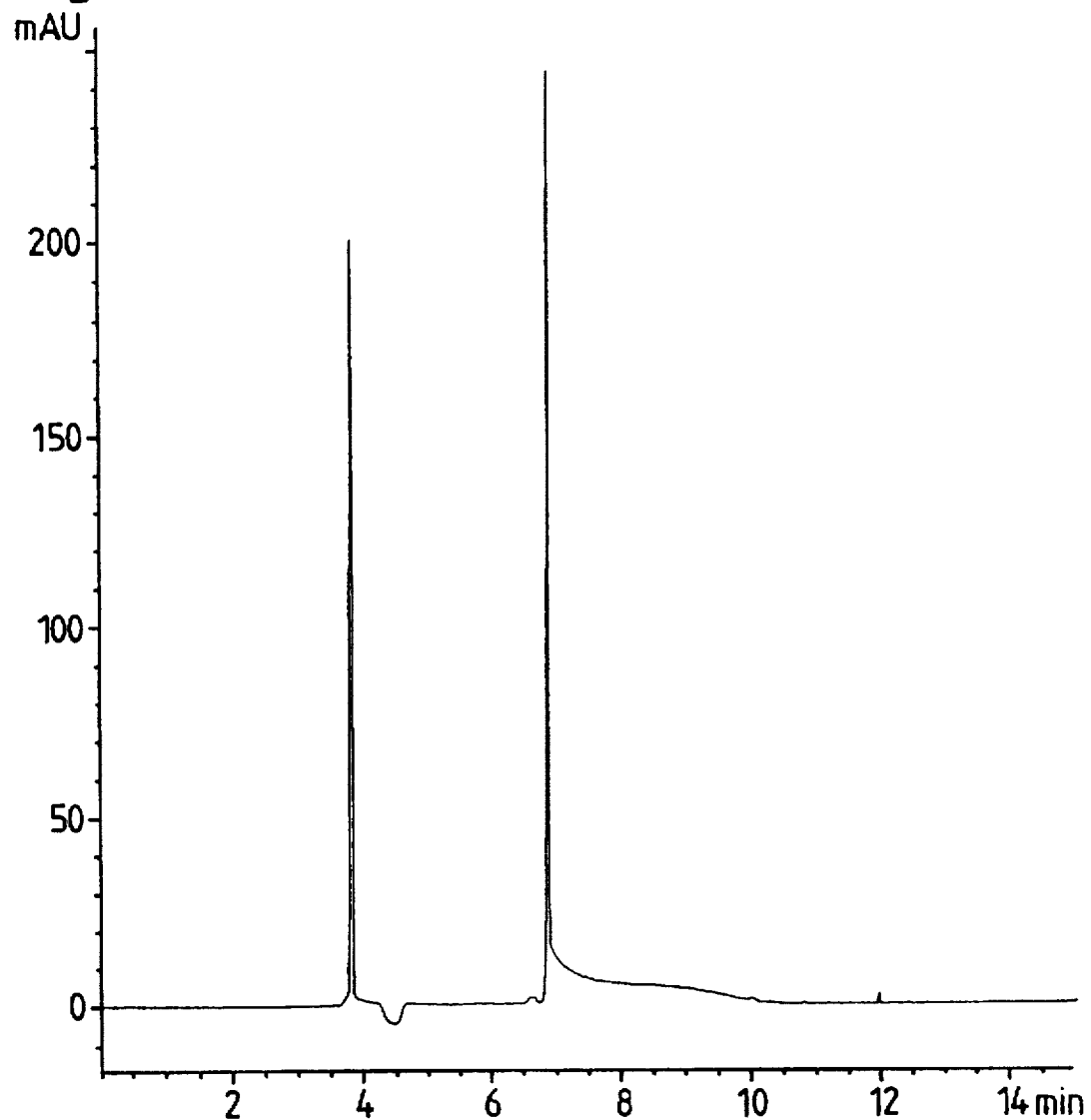
Figure 6:
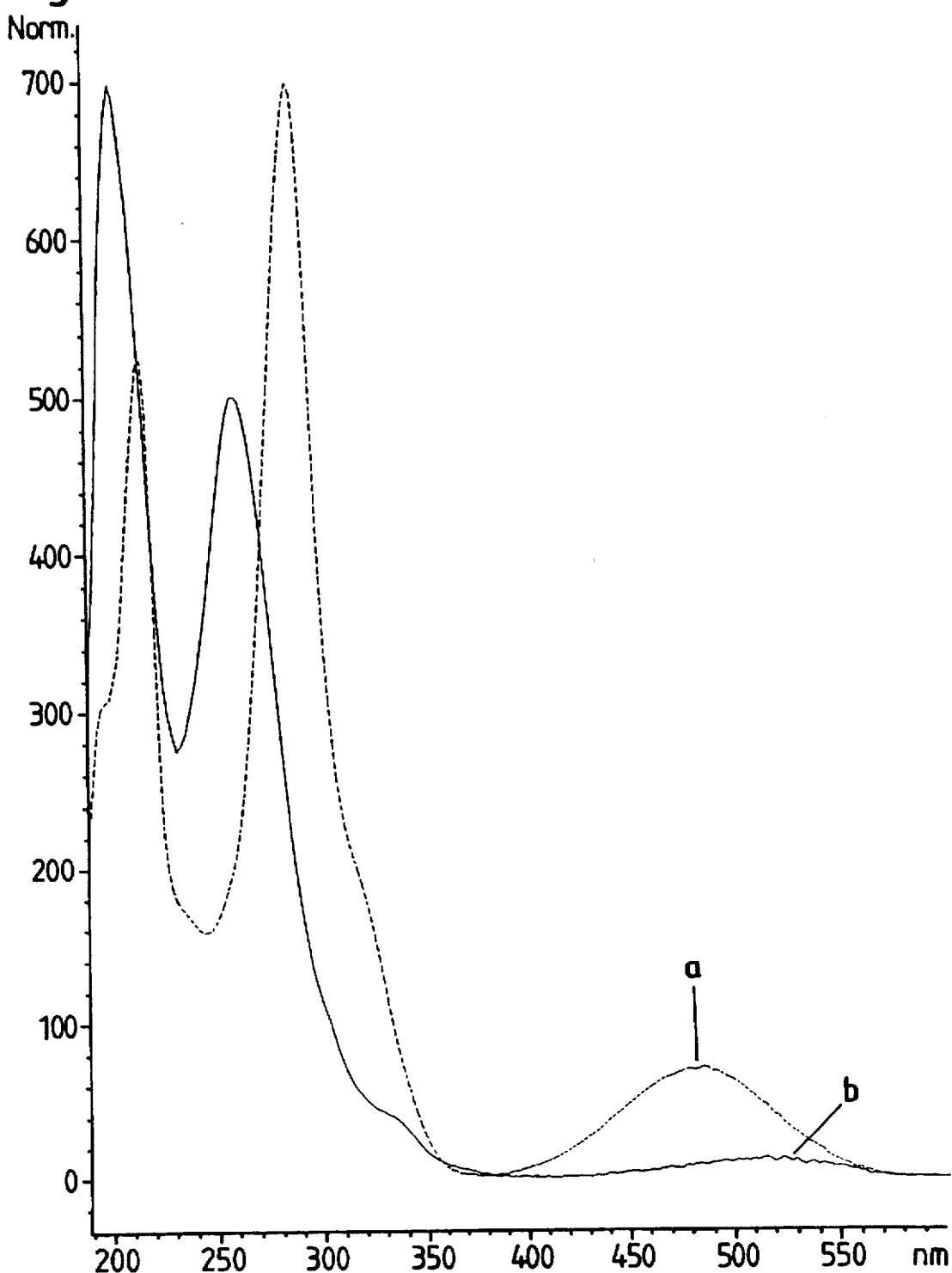

Example 2.1: Separation and Identification of Stained Foot-and-Mouth Viruses using UV Detection The reference sample of foot-and-mouth virus from Example 1.1 (300 μg/ml) with 10 μg/ml of ethidium bromide (see, for example, R. P. Haugland, Handbook of fluorescent probes and research chemicals, Molecular Probes, Inc. 1992) was incubated for 30 minutes at room temperature and then investigated by means of CE (the conditions were as shown in Table 2). Two signals could be detected (FIG. 5). The UV/VIS spectra in the CE are represented in FIG. 6. The signal at 3.8 min represented excess ethidium bromide from the incubation (also reaffirmed by coinjection). The peak at 6.9 min showed absorption maxima at 200, 257 (intensive) and 510 nm (weak). The long-wave shift of the visible absorption maximum from free ethidium bromide (495 to 510 nm) is characteristic for the intercalation with nucleobases. The position of the virus signal in the electropherogram was virtually unshifted by the incorporation of ethidium bromide (cf. FIGS. 1 and 5).

The separation and identification of stained viruses could be successfully demonstrated from the example of ethidium bromide.

Example 2.2: Fluorescence Detection of Stained Foot-and-Mouth Virus

Figure 7:
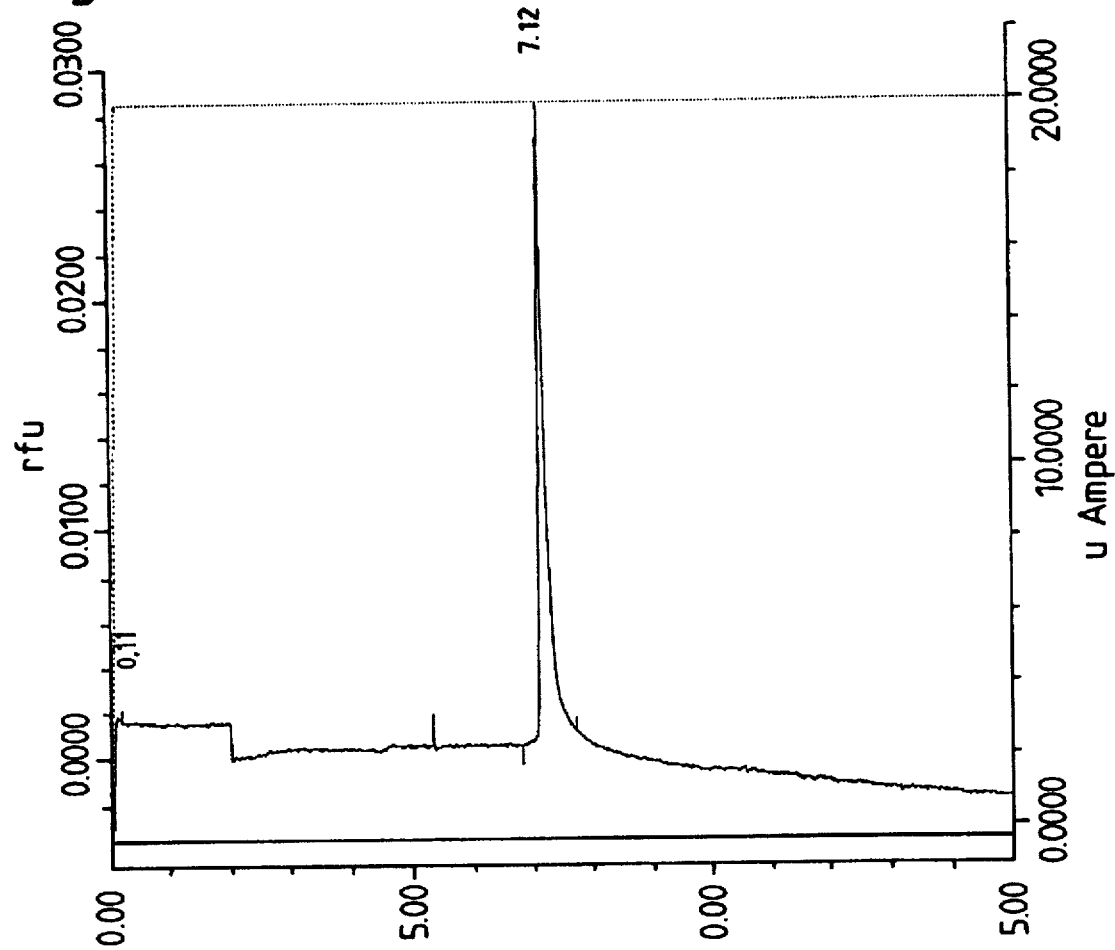

The foot-and-mouth concentrate sample from Example 1.2, after 1:15 dilution with the separating buffer (Table 5) was incubated with 1,1'-(4,4,7,7-tetramethyl-4,7-diazaundecamethylene)bis-4-[3-methyl-2,3-dihydromethyl (benzo-1,3-oxazole)-2-methylidene]-quinolinium tetraiodide (YOYO) (1 μmolar) for 30 minutes at room temperature and then measured using CE (the measuring conditions are shown in Table 5). Only one single signal could still be seen in the concentrate (FIG. 7). The inherent fluorescence of YOYO was so small that free YOYO could no longer be detected by fluorescence detection. The remaining signals from the concentrate were not visible by this nucleotide-specific detection (compare UV detection of the identical sample in FIG. 3). The strong shift in migration time arose from differing capillary lengths and strengths (cf. Table 3 and Table 5).

TABLE 5

Measuring conditions for CE separation using fluorescence detection of foot-and-mouth reference samples using CE

| | |
|---|---|
| Capillary: | Fused silica capillary, 50 μm internal diameter, 47 cm length, 40 cm to the detector |
| Voltage: | 20 kV |
| Buffer: | Tris (25 mmolar), glycine (192 mmolar), sodium dodecyl sulphate (50 mmolar), pH 8.5 |
| Temperature: | 25° C. |

TABLE 5-continued

Measuring conditions for CE separation using fluorescence detection of foot-and-mouth reference samples using CE

| | |
|---|---|
| Detection: | LIF (argon) EX 488, EM 520 nm, Gain 100 |
| Injection: | Pressure (10 sec × 10³ Pa) |
| Rinsing of the capillary prior to injection: | 1. NaOH (0.1 N, 1 min, 5 × 10⁴ Pa) <br> 2. Buffer (3 min, 5 × 10⁴ Pa) |

Example 2.3: Separation and Identification of Orf Viruses using Fluorescence Detection The orf virus belongs to the group of the Parapox viruses. The virus is composed of a double-stranded DNA having approx. 140,000 base pairs, which is enclosed together with a large number of enzymes in a protein coat (core) and a further lipoprotein coat. It is therefore a so-called coated virus. The virus particle has the shape of a brick of approx. 400×200×200 nm in size and therefore ranks among the largest viruses in general. By virtue of the very different surface structure and size from that of foot-and-mouth virus, the breadth of application of the new method should be demonstrated by this Example.

The virus was isolated in the following manner (Table 6):

TABLE 6

| Isolation of orf virus | |
|---|---|
| Virus propagation | BK-clone 3 A monolayer cells in stacked tanks; virus harvest 150 l after cell lysis |
| Preliminary purification | Preclarification of the raw virus suspension by low-speed continuous centrifugation |
| Inactivation | β-propiolactone |
| Second purification step | Low-speed continuous centrifugation |
| Purification of reference samples | Density-gradient centrifugation in sodium tartrate for isolation of the virus band |

A direct UV spectroscopic identification is ruled out owing to the size of the virus, as at this size light scattering occurs in the UV. Moreover the orf sample, even after the second purification step (Table 6), is present in too low a concentration for UV detection. The virus can therefore be identified only by fluorescence detection.

Figure 8A:
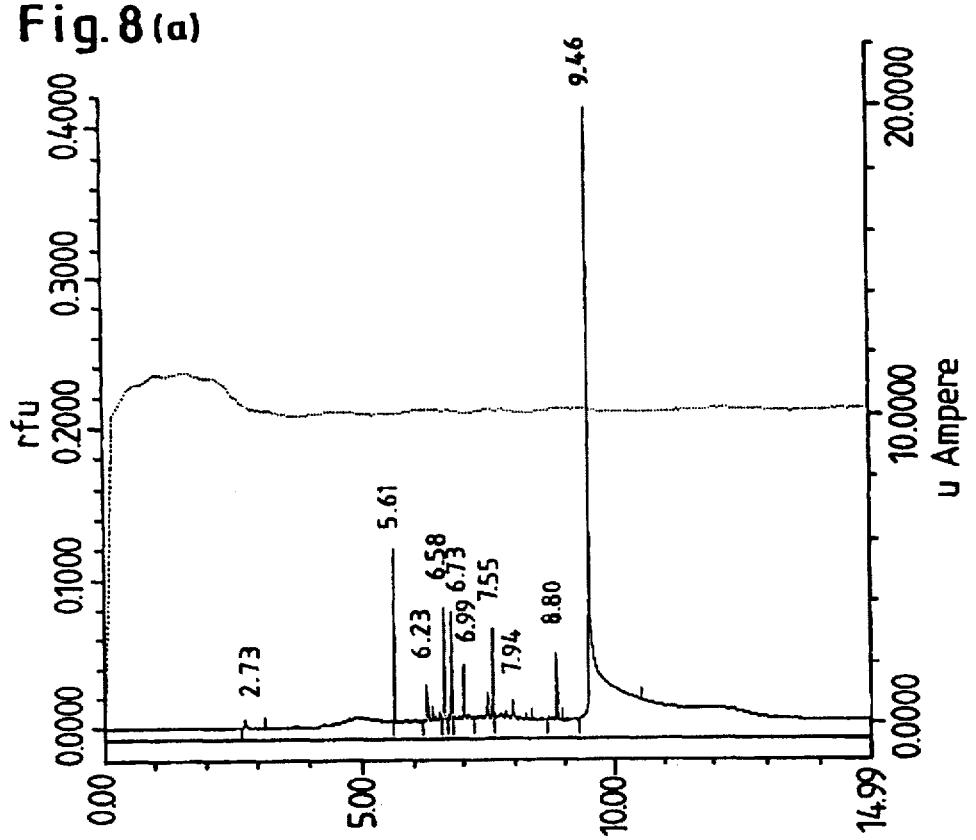

Baypamun® (commercially available immunomodulator from the firm Bayer AG, made from inactivated orf viruses) was incubated with YOYO (1 µmolar) for 30 minutes at room temperature and then separated using CE (the measuring conditions are as shown in Table 5, but the separating buffer was Tris/borate, 100 mmolar, pH 8.5). At 2.73 min the excess YOYO could be seen as an extremely small peak (FIG. 8a). At 9.46 min the orf virus could be isolated and detected as an individual signal. The spikes occurring in addition were probably caused by the sample matrix, as in this region of the electropherogram a broad absorption could be measured by means of UV. The spikes always occurred during this measurement. The position of the spikes was not however reproducible.

Thus an extremely large coated virus could be directly identified by means of fluorescence detection. A further identification of the signal is described in Example 3.2.

Example 2.4: Separation and Identification of the Core of the Orf Virus

As already stated in the introduction to Example 2c, the size and the concentration of orf prevent the direct detection by UV. As it is moreover a coated virus, attempts should be made to investigate the inner protein coat including the enclosed DNA (core).

Figure 9A:
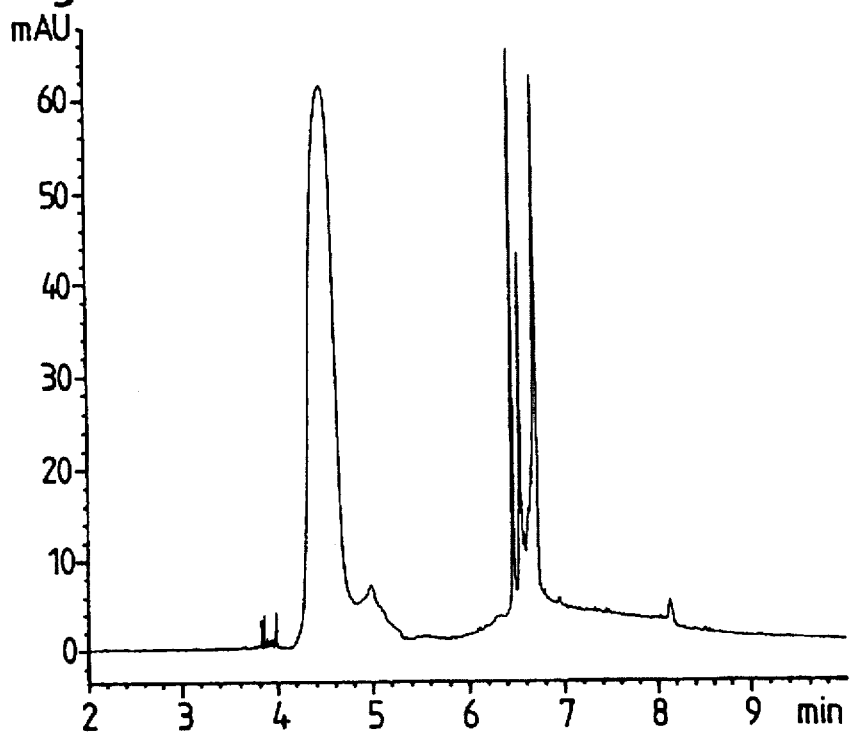
Figure 9B:
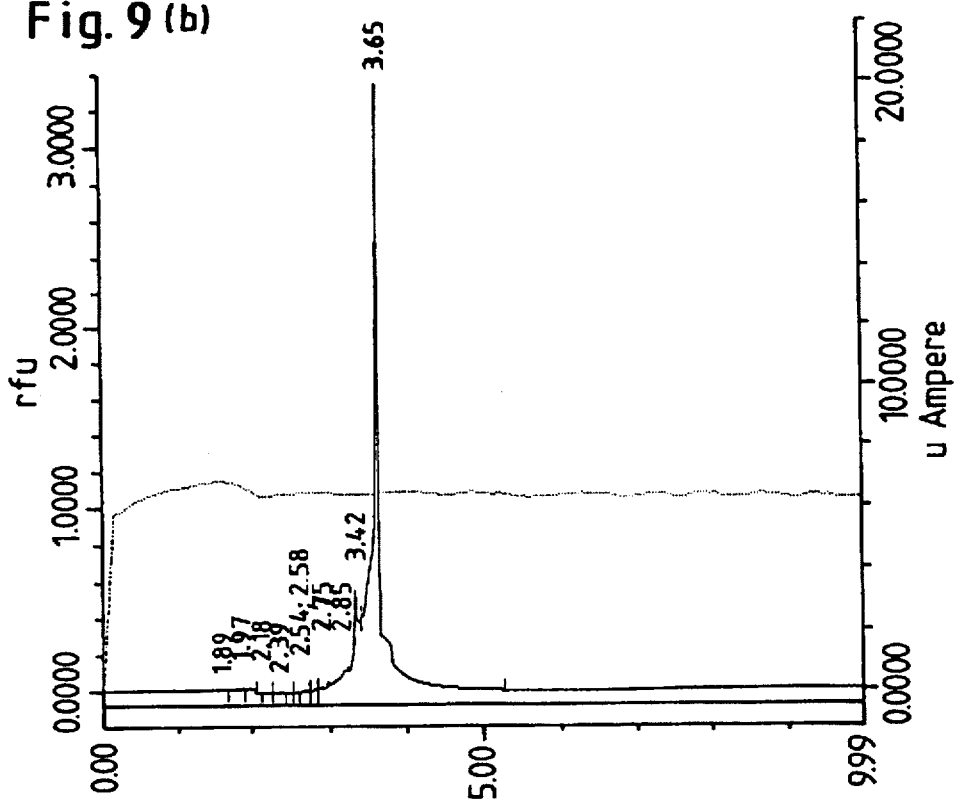

Baypamun was freed from its lipoprotein membrane according to a modified specification [9] by shaking with NP-40 (1%, 1 hour, 37° C.) and the core was pelleted by density-gradient centrifugation (sucrose 36%, PBS 150 mmolar, 225.000 g, 1 hour). The sample thus concentrated was incubated with YOYO (concentration 1 µmolar) for 30 minutes at room temperature and then measured by CE using DAD (the measuring conditions are shown in Table 2). The electropherogram at 257 nm (FIG. 9a) showed a broad band at 4.5 min, which could be identified as excess YOYO. Of the three intensive signals between 6.4 and 6.8 min, only the last signal showed the absorption maximum at 495 nm typical for intercalating YOYO (FIG. 10). The identical sample was subsequently also further investigated by LIF detection. The measuring conditions corresponded to those of Table 5, except that sodium dodecyl sulphate was dispensed with in the separating buffer (same buffer as in the UV detection). The absolute migration time was clearly shifted by the change of capillary and of field strength, as compared with the UV measurement (FIG. 9). The excess YOYO could be identified as a tiny peak at 1.9 min. Of the three UV signals, only the stained product (the core) could be detected. In addition, by means of fluorescence detection an increase in the sensitivity by a factor of 10⁴ could be achieved as compared with the UV detection of the unstained core.

By means of these experiments it could be proved that not only complete viruses (coated or uncoated) can be directly identified but also altered virus particles, which can be produced from coated viruses by removal of the lipoprotein membrane.

The achievement of a further improvement by an additional specification of the virus signals is described in the next Section.

3. Additional Specification of the Virus Particles During (in) the Capillary Electrophoretic Separation Through Interactions with Antibodies Investigations were made as to how known viruses can be clearly differentiated by means of specific antibodies (MABs). Here the entire established immunological differentiation of viruses in direct combination with the separation of viruses in CE is available.

General Description of the Method

The sample to be analysed is:
a) incubated with the antibody (MAB, antisera, mixtures of antibodies, labelled antibodies) and then separated and analysed in accordance with the methods described above or
b) the antibodies (MAB, antisera, mixtures of antibodies, labelled antibodies) are added to the separating buffer and the virus is separated and analysed in accordance with an affinity capillary electrophoresis having regard to the methods described above.

The specific interaction of the antibody (antibodies) with the virus can be detected either through a shift in migration time or through a decrease in the intensity of the virus signal.

Examples

In the following examples the virus to be investigated was incubated with specific antibodies and then separated using CE. The stability of the antibody-antigen binding is great enough for it to survive the separation in undenatured solvents as an intact complex. Consequently it is possible to measure the difference in the migration time between the free virus and the virus-antibody complex from different separations.

Figure 8B:
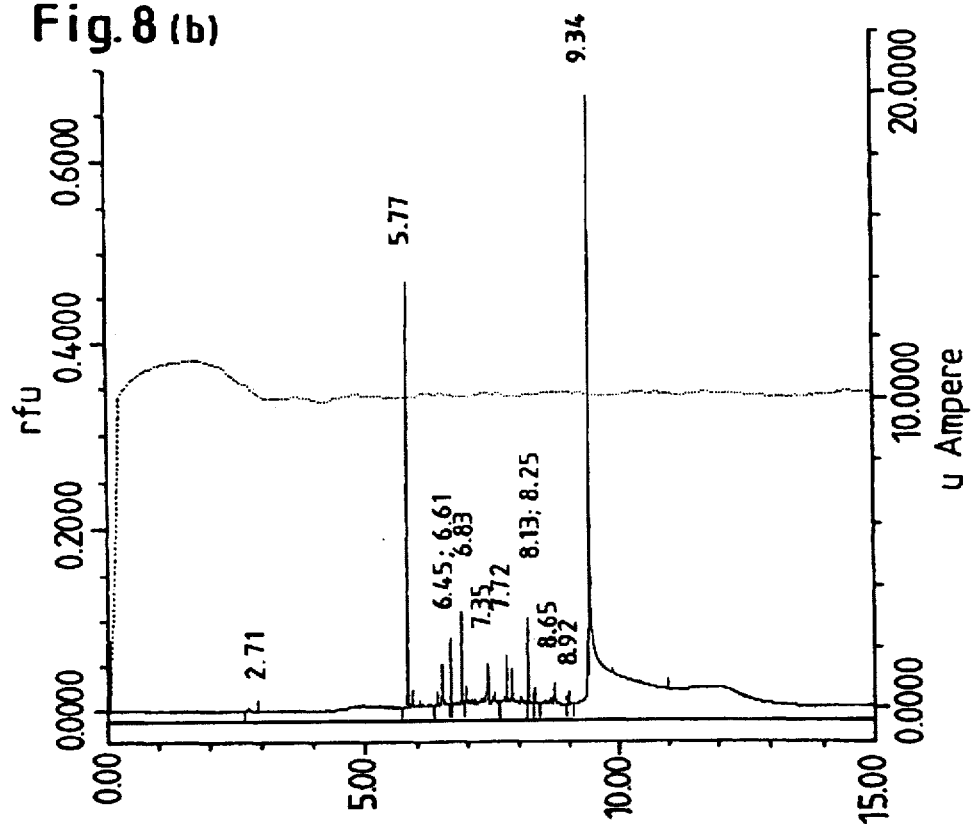

Example 3.1: Specification of the Orf Virus Signal By Shift in Migration Time Using Monoclonal Antibodies The orf sample from Example 2.3, following the incubation with the stain, was in addition mixed with an anti-orf antibody (MAB) (2 µg/ml) and incubated for a further 30 minutes at room temperature. The measuring conditions were identical with those in Example 2.3. The electropherogram is shown in FIG. 8b. The electropherogram differs from that of the free virus solely in the position of the virus signal (FIG. 8). The fluorescence signal of the orf virus shifted, owing to the binding of the MAB, from 9.46 min to 9.34 min; the shift was reproducible. A greater shift was not to be expected because of the size of the virus. As this virus ranks among the largest viruses in general, the breadth of application of this method could be demonstrated by this experiment. The shift of the signal proves that the observed fluorescence signal is in fact of viral origin and, when the MAB is of sufficient specificity, the signal can also be assigned to the orf virus. In the next Example it will be shown that a distinctly greater shift can be obtained in the case of smaller viruses.

Example 3.2: Specification of the Foot-and-Mouth Virus Signal by Shift in Migration Time Using Monoclonal Antibodies The reference sample from Example 1.1 (100 µg/ml), which corresponds to the strain of virus $O_{1k}$ ($O_1$-Kaufbeuren) known from the literature, was mixed with different anti-foot-and-mouth $O_1$ MABs (1–10 µg/ml) and, with anthraquinone-1-sulphonic acid as internal standard (2 µg/ml), and incubated for 30 minutes at room temperature and measured under the conditions given in Table 2. The relative migration times ($t_{mr}$) of the incubated samples were compared with the $t_{mr}$ of the pure virus, samples of which were prepared in the same way and under identical measuring conditions (FIG. 11a). The dark bars show the $t_{mr}$ of the pure virus and the light bars show the $t_{mr}$ of the viruses incubated with antibodies. The different MABs are recorded on the x-axis and were measured in the sequence from left to right. A slight initial fall in the $t_{mr}$ is apparent in the dark bars and can be attributed to a not yet completely equilibrated capillary. For antibodies 24, 37, 48 and 99, a to some extent marked shift in the $t_{mr}$ could be observed. The reference sample investigated could thus be assigned serologically to the strain $O_1$. The extent of the shift is not a direct measure of the affinity of the MAB. The shift is determined by the migration behaviour and by the number of bound antibodies. The positively acting MABs all showed a shift of the $t_{mr}$ of between 0.05 and 0.13. Antibody 75 produced no significant shift of the $t_{mr}$ and an identification of the virus by means of this antibody was not therefore demonstrable. Either the migration times of MAB 75 and foot-and-mouth $O_{1k}$ were too alike, or MAB 75 does not recognise this strain of virus.

In order to verify the MAB binding to foot-and-mouth $O_{1k}$, the same antibodies were incubated with foot-and-mouth $O_{1m}$ under identical conditions and measured by way of comparison. ($O_{1m}$ ($O_1$-Manisa) is another strain of virus known from the literature). Here also the initial fall in the $t_{mr}$ is apparent in the dark bars. After incubation with the MABs (light bars) only MAB 75 showed a significant shift of 0.10. This MAB accordingly clearly recognises foot-and-mouth $O_{1m}$. Since foot-and-mouth $O_{1m}$ and foot-and-mouth $O_{1k}$ were detected at a very similar $t_{mr}$, a non-recognition of foot-and-mouth $O_{1k}$ owing to similar migration times of virus and virus-MAB complex is ruled out. MAB 75 could therefore be confirmed as anti-foot-and-mouth $O_{1m}$, whereas all other MABs recognise only foot-and-mouth $O_{1k}$. The remaining MABs shift foot-and-mouth $O_{1m}$ by 0.02 at most, which has to be regarded as non-specific in comparison with FIG. 11a.

From the measurements described above it is definitely proved that viruses and viral particles (inactivated viruses, cores) can be directly analysed and detected using the newly developed method. Even complex sample matrices (raw foot-and-mouth concentrate, Baypamun) do not interfere with the analysis. The breadth of application of this method for very different viruses could be demonstrated by the Examples of the small Picornaviruses (foot-and-mouth), the large coated orf virus and the core thereof. By means of nucleotide-specific staining reagents, viruses could be specifically detected by both UV and by fluorescence. In this connection extreme increases in sensitivity could be observed. The viruses or viral particles can be specifically detected by complexing with antibodies. The antibody recognition could be documented even in the presence of staining reagents. A complete analytical repertoire for the general identification of viral components in complex matrices is thus provided. This method therefore has considerable potential for future use, both for process control and for the diagnosis of viruses.

Technical References

[1] Engelhardt, H., Beck, W., Kohr, J. and Schmitt, T. Angew. Chem. 1993, 105, 659–680

[2] Kuhr, W. G. and Monnig, C. A. Anal. Chem. 1992, 64, 389R–407R

[3] W. M. Hurni and W. J. Miller, J. Chromato. 1991, 559, 337–343

[4] R. Bartzatt, J. Histotechnol. 1987, 10, 95–96

[5] Haugland, R. P., Handbook of fluorescent probes and research chemicals (Larison, K. D. Ed.) Molecular Probes, Inc. 1992

[6] Zuh, H., Clark, S. M., Benson, S. C., Pye, H. S., Glazer, A. N. and Mathies, R. A. Anal. Chem. 1994, 66, 1941–1948

[7] Heegaard, N. H. H. and Robey, F. A. Anal. Chem. 1992, 64, 2479–2482

[8] Chu, Y.-H., Avila, L. Z., Biebuyck, H. A. and Whitesides, G. M. J. Org. Chem. 1993, 58, 648–652

[9] Paoletti, E., Rosemund Hornbeak, and Moss, B. J. Bio. Chem. 1974, 249, 3273–3280

We claim:

1. Method for the non-destructive analytical detection or quantification of viruses or viral particles in a liquid sample matrix containing organic or inorganic minor constituents, protein moieties, nucleotides or other viruses, comprising a) using a body liquid as a sample matrix for diagnostically detecting viruses or viral particles contained therein b) separating the viruses or the viral particles from the protein moieties and/or nucleotides in the body liquid using a capillary electrophoresis system to obtain electrophoretical fractions wherein the capillary electrophoresis system is provided with a separating buffer to which is added a DNA/RNA-binding reagent, so that the virus or the viral particles in the body liquid introduced into the capillary electrophoresis system are stained during the electrophoretical separation, c) recording an electropherogram associated with the electrophoretical fractions and d) identifying the fractions as virus peaks by interpretation of the data in the electropherogram.

2. Method according to claim 1, which comprises the further step of adding a reference sample of a known virus or of a known viral particle to the body liquid for the identification of the fractions.

3. Method according to claim 1, which further comprises incubating the body liquid with said RNA/DNA-binding, spectroscopically identifiable stain.

4. Method for the non-destructive analytical detection or quantification of viruses or viral particles in a liquid sample matrix containing organic or inorganic minor constituents, protein moieties, nucleotides or other viruses, comprising a) using a body liquid as a sample matrix for diagnostically detecting viruses or viral particles contained therein b) separating the viruses or the viral particles from the protein moieties and/or nucleotides in the body liquid using a capillary electrophoresis system to obtain electrophoretical fractions wherein the capillary electrophoresis system is provided with a separating buffer to which is added a DNA/RNA-binding reagent which is non-fluorescent or which adds minimal fluorescence in this free state but which generates a significant fluorescence signal when incorporated in the viruses or the viral particles, so that the viruses or the viral particles in the body liquid introduced into the capillary electrophoresis system are stained during the electrophoretical separation, c) recording an electropherogram associated with the electrophoretical fractions and d) identifying the fractions as virus peaks by interpretation of the data in the electropherogram.

5. Method according to claim 4, which further comprises incubating the body liquid with said RNA/DNA-binding, spectroscopically identifiable stain.

\* \* \* \* \*